United States Patent [19]

Yeh

[11] Patent Number: 5,136,065
[45] Date of Patent: Aug. 4, 1992

[54] PROPARGYL ESTERS OF CARBOXYLIC ACIDS CONTAINING CONJUGATED ETHYLENIC UNSATURATION AND ORGANOSILICON COMPOUNDS DERIVED FROM SAME

[75] Inventor: Ming-Hsiung Yeh, Midland, Mich.

[73] Assignee: Dow Corning Corporation, Midland, Mich.

[21] Appl. No.: 814,524

[22] Filed: Dec. 30, 1991

[51] Int. Cl.$^5$ .............................. C07F 7/08; C07F 7/10
[52] U.S. Cl. ...................................... 556/415; 556/440
[58] Field of Search ................................ 556/440, 415

[56] References Cited

U.S. PATENT DOCUMENTS

| | | | |
|---|---|---|---|
| 4,010,232 | 3/1990 | Arai | 556/440 X |
| 4,554,339 | 11/1985 | Hockmeyer et al. | 556/440 X |
| 4,562,278 | 12/1985 | Hill | 556/440 X |
| 4,940,766 | 7/1990 | Gay et al. | 556/440 X |

OTHER PUBLICATIONS

European Polymer Journal, vol. No. 7, pp. 639–645, (1988).

Primary Examiner—Paul F. Shaver
Attorney, Agent, or Firm—Robert Spector

[57] ABSTRACT

Novel propargyl esters are prepared by a base catalyzed condensation reaction of propargyl esters of carboxylic acids containing a labile hydrogen atom at the alpha position relative to the carboxy group, and a terminal aromatic hydrocarbon radical that is linked to the carboxy group through a sequence of carbon atoms containing at least one carbon-to-carbon double bond. If more than one of these double bonds are present they form a conjugated sequence. Novel organosilicon compounds are prepared by reacting these propargyl esters with an organohydrogensilane or an organohydrogensiloxane. The organosilicon compounds undergo a reversible crosslinking reaction in the presence of ultraviolet light.

13 Claims, No Drawings

PROPARGYL ESTERS OF CARBOXYLIC ACIDS CONTAINING CONJUGATED ETHYLENIC UNSATURATION AND ORGANOSILICON COMPOUNDS DERIVED FROM SAME

BACKGROUND OF THE INVENTION

1. Field of the Invention

This invention relates to a novel class of organosilicon compounds. More particularly, this invention relates to a class of organosilicon compounds derived from 1) organohydrogensilanes or organohydrogensiloxanes and 2) novel propargyl esters of carboxylic acids containing a terminal aromatic hydrocarbon radical, where the carbopropynoxy group of the ester and the aromatic hydrocarbon radical are separated by at least two adjacent ethylenically unsaturated carbon atoms. If more than two of these carbon atoms are present they form a sequence of conjugated ethylenic double bonds.

2. Background Information

The photo-induced crosslinking of polyorganosiloxanes obtained by reacting organohydrogensiloxanes with the reaction product of vinyldimethylchlorosilane with an alkali metal salts of cinnamic, beta-(2-furyl) acrylic or alpha-cyano-beta-styryl acrylic (also referred to as 2-cyano-5-phenyl-2-4-pentadienecarboxylic) acid is described by R. Mercier, X. Coqueret and coworkers in the European Polymer Journal, vol. 24, No. 7, pages 639–645 (1988).

In addition to producing quantities of insoluble gel resulting from multiple crosslinks between adjacent molecules, the non-crosslinked by-products produced using the method of Mercier et al. are difficult to separate.

An objective of this invention is to provide novel propargyl esters of the ethylenically unsaturated carboxylic acids described in the aforementioned article by Mercier et al. A second objective of this invention is to provide organosilicon derivatives of these esters that form crosslinked materials upon irradiation with ultraviolet light. Another objective of this invention is to employ these propargyl esters in a method for preparing photo-crosslinkable organosilicon compounds that avoids the shortcomings of the method described by Mercier et al.

SUMMARY OF THE INVENTION

The present inventor discovered that the reaction of propargyl esters of carboxylic acids containing a sequence of at least two conjugated ethylenic double bonds with silicon-bonded hydrogen atoms occurs exclusively at the propargyl group. Both the propargyl esters and their organosilicon derivatives are novel compounds.

DETAILED DESCRIPTION OF THE INVENTION

This invention provides organosilanes exhibiting the molecular formula $$QR^1{}_3Si \qquad (1)$$

and organosiloxanes containing units of the formula $$QR^1{}_aSiO_{(3-a)/2} \qquad (2)$$

where Q represents the radical $$R^2(CH=CH)_n-CH=CR^3C(O)OCH_2CH=CH-,$$

each $R^1$ is individually selected from the group consisting of unsubstituted and substituted monovalent hydrocarbon radicals, $R^2$ represents an aryl, alkoxyaryl or alkaryl radical, $R^3$ is $-C\equiv N$ or $-C(O)OR^4$ where $R^4$ is hydrogen or an unsubstituted monovalent hydrocarbon radical selected from the same group as $R^1$, a is 0, 1 or 2 and n is 0 or a positive integer, with the proviso that n can be 0 only when $R^2$ represents a naphthyl radical.

This invention also provides a method for preparing the present compounds by the platinum-catalyzed reaction of an organohydrogensilane or an organohydrogensiloxane with a novel class of propargyl esters exhibiting formula 3

$$R^2(CH=CH)_n-CH=CR^3C(O)OCH_2C\equiv CH \qquad (3)$$

where $R^2$, $R^3$ and n are defined in the preceding paragraph.

This invention also provides the novel propargyl esters represented by formula 3.

The present inventor discovered that the platinum-catalyzed hydrosilylation reaction of an organohydrogensiloxane occurs exclusively at the propargyl group, resulting in a high yield of the desired product containing units of the formula $R^2(CH=CH)_n-CH=CR^3C(O)OCH_2CH=CHSiR^1{}_aSiO_{3-a/2}$ rather than the expected mixture of products resulting from occurrence of the hydrosilylation reaction at the carbon-carbon double bonds or at the carbonyl portion of the carboxyl group as reported in the aforementioned articles by Mercier et al.

The organosilicon compounds of the present invention undergo an intermolecular coupling reaction in the presence of ultraviolet radiation in the range of 300 to 400 nm that is believed to involve formation of cyclobutane rings by pairs of ethylenically unsaturated carbon atoms on adjacent molecules of the compound. This reaction is reported in the aforementioned articles by Mercier et al. and can be depicted as

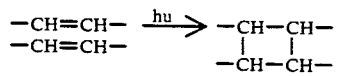

A major portion, typically at least 50 percent, of the intermolecular bonds formed during this reaction can be broken by exposing the reaction product to ultraviolet radiation in the range from 200 to 260 nm, thereby converting at lest a portion of the intermolecularly bonded compound to the original organosilicon compound represented by formula 1 or 2.

The substituent represented by $R^3$ in the present compounds can be a cyano ($-C\equiv N$) group or a group represented by the formula $-C(O)OR^4$ where $R^4$ is hydrogen or an unsubstituted monovalent hydrocarbon radical.

Unsubstituted monovalent hydrocarbon radicals that can be represented by $R^1$ and $R^4$ include but are not limited to alkyl radicals containing from 1 to 10 carbon atoms such as methyl, ethyl and propyl, cycloalkyl radicals such as cyclohexyl, aryl such as phenyl, alkaryl such as tolyl and xylyl and aralkyl such as benzyl. Substituents that can be present on $R^1$ include but are not limited to halogens such as chlorine, bromine and fluorine. Most preferably $R^1$ is methyl, phenyl or 3,3,3-trifluoropropyl and $R^4$ is hydrogen.

$R^2$ represents an aryl, alkoxyaryl or alkaryl radical such as phenyl, o-, m-, or p-methoxyphenyl, naphthyl or tolyl. In preferred embodiments of the present compounds $R^2$ is phenyl, o-, m-, or p- methoxyphenyl or naphthyl and n is 0 or 1, this preference being based on the availability of the starting materials used to prepare this embodiment and the high yield of desired product in the absence of undesirable by-products when the propargyl ester is prepared using the Knoevenagel condensation reaction described in the following section of this specification.

Preparation of the Propargyl Ester

Formula 3

A preferred class of the esters represented by formula 3 can be prepared using the Knoevenagel reaction, a base-catalyzed condensation between an aldehyde and the ester of an acid containing a labile hydrogen atom in the alpha position relative to the carbonyl group. This reaction is typically catalyzed by a base, and can be illustrated by the general equation

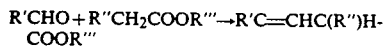
$$R'CHO + R''CH_2COOR''' \rightarrow R'C=CHC(R'')H\text{-}COOR'''$$

where R', R'' and R''' represent monovalent hydrocarbon radicals.

The reaction used to prepare the propargyl ester of formula 3 is represented by the equation

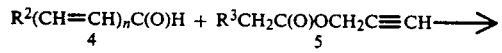
$$R^2(CH=CH)_nC(O)H + R^3CH_2C(O)OCH_2C\equiv CH \longrightarrow$$
$$\underset{4}{\phantom{X}} \qquad \underset{5}{\phantom{X}}$$

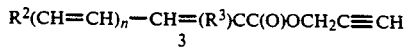
$$R^2(CH=CH)_n-CH=(R^3)CC(O)OCH_2C\equiv CH$$
$$\underset{3}{\phantom{X}}$$

The reactants used to prepare the propargyl ester represented by formula 3 are the propargyl ester of a carboxylic acid containing a labile hydrogen atom on the alpha carbon relative to the carbonyl group (formula 5) and an ethylenically unsaturated aldehyde containing a terminal aromatic hydrocarbon radical represented by $R^2$ (formula 4). Preferably n is 0 or 1.

The Ethylenically Unsaturated Aldehyde Reactant

Formula 4

The ethylenically unsaturated aldehyde used in the Knoevenagel reaction can be represented by formula 4

$$R^2(CH=CH)_nC(O)H \qquad (4)$$

where $R^2$ represents an aryl radical such as phenyl or naphthyl and the value of n is 0 or a positive integer, with the proviso that n can be 0 only when $R^2$ represents a naphthyl radical. Preferably n is 0 or 1.

Suitable aldehydes represented by formula 4 contain an aromatic hydrocarbon radical at the terminal position and include but are not limited to cinnamaldehyde and products of an aldol condensation reaction between (6) cinnamaldehyde, o- or p-methoxy cinnamaldehyde, benzaldehyde, naphthaldehyde or other aldehyde containing an aromatic hydrocarbon radical at the terminal position and (7) an ethylenically unsaturated aliphatic aldehyde such as crotonaldehyde or acrolein.

When the carbonyl group of one of the aldehydes is bonded to an aromatic hydrocarbon ring structure or separated from the ring structure by a —CH=CH— group as in cinnamaldehyde, typically only one condensation product is formed.

The ethylenically unsaturated carbon atoms of the unsaturated aliphatic aldehyde 7 are adjacent to the aldehyde group [—C(O)H]. If both the aldehydes (6 and 7) used in the aldol condensation contain ethylenically unsaturated carbon atoms in this position, this will maximize the number of conjugated double bonds present in the reaction product.

The aldol condensation reaction between cinnamaldehyde (6a) and crotonaldehyde (7a) can be represented by the following equation, where Ph represents a phenyl radical.

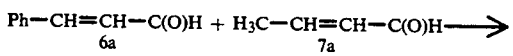
$$Ph-CH=CH-C(O)H + H_3C-CH=CH-C(O)H \longrightarrow$$
$$\underset{6a}{\phantom{X}} \qquad \underset{7a}{\phantom{X}}$$

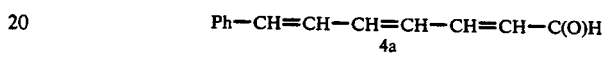
$$Ph-CH=CH-CH=CH-CH=CH-C(O)H$$
$$\underset{4a}{\phantom{X}}$$

If desired it should be possible to repeat the condensation reaction to increase the number of sequential conjugated double bonds in the ethylenically unsaturated aldehyde that is subsequently reacted with the ester reactant represented by formula 5 to prepare the propargyl esters of the present invention represented by formula 2.

The Propargyl Ester Reactant (5)

The propargyl ester used in the Knoevenagel reaction contains a labile hydrogen atom on the carbon atom adjacent to the carboxyl group.

The Knoevenagel condensation reaction between the ester (5) and the aromatic aldehyde (4) to form the propargyl ester represented by formula 3 is typically conducted at ambient temperature or below in the presence of a catalytic amount of an amine. Suitable amine catalysts include but are not limited to aliphatic amines, aromatic amines such as aniline and p-nitroaniline. Heterocyclic amines such as piperidine are preferred.

The condensation reaction is typically carried out with the reactants dissolved in a common solvent, particularly when the reaction product is a solid. Useful solvents include but are not limited to cyclic ethers such as tetrahydrofuran and dioxane.

Preparation of the Silylated Propargyl Ester

The organosilicon compounds of this invention can be prepared by the reaction of an organohydrogensilane or an organohydrogensiloxane with the propargyl group of the ester prepared as described in the preceding section of this specification and represented by formula 3.

$$R^3(CH=CH)_n-CH=CR^2C(O)OCH_2C\equiv CH \qquad (3)$$

The reaction between silicon-bonded hydrogen atoms and a carbon-carbon double bond or triple bond is referred to as a hydrosilylation reaction and is typically catalyzed by a metal from the platinum group of the periodic table or a compound of such a metal. In addition to platinum the platinum group of metals includes rhodium and palladium. To provide the desired selectivity of reaction at the actylenic carbon atoms of the propargyl ester it is preferred to use platinum or a compound of this metal. Chloroplatinic acid, and more particularly complexes of chloroplatinic acid with liquid ethylenically unsaturated organosilicon compounds such as sym-tetramethyldivinyldisiloxane, are preferred catalysts for the reaction of the propargyl ester with the organosilicon compound containing silicon-bonded hydrogen atoms. This preference is based on the selectivity of these catalysts in limiting the site of the hydrosilylation reaction to the propargyl group of the ester represented by formula 3 and the high yield of the desired organosilicon compound.

The propargyl ester 3 and the organohydrogensilane or organohydrogensiloxane are preferably used in substantially equimolar amounts to avoid undesirable side reactions between the silicon bonded hydrogen atoms and the conjugated carbon-carbon double bonds present in the acid portion of the propargyl ester.

The hydrosilylation reaction is typically carried out in the presence of a solvent that will not participate in this reaction. Preferred solvents include but are not limited to liquid aromatic and saturated aliphatic hydrocarbons.

While the hydrosilylation reaction will proceed at room temperature, the reaction mixture is preferably heated at between 70° and 110° C. to increase the rate of the reaction. The preferred temperature will depend upon a number of variables, including the type of organohydrogensilane or organohydrogensiloxane used. The course of the reaction can conveniently be followed using infrared spectroscopy to observe the decreasing concentration of the propargyl ($-H_2$-$C-C\equiv CH$) and SiH groups as the reaction proceeds.

Preferred organohydrogensiloxanes include but are not limited to symmetrical tetraalkyldihydrogendisiloxanes, resinous organosiloxane copolymers containing phenylsilsesquioxane ($PhSiO_{3/2}$) and dimethylhydrogensiloxy units, and substantially linear organopolysiloxanes wherein at least a portion of the repeating units are represented by the formula $R^1HSiO$, where $R^1$ represents an unsubstituted or substituted monovalent hydrocarbon radical as defined in the preceding specification, any remaining non-terminal units are $R^1_2SiO$, and the terminal units are triorganosiloxy or diorganohydrogensiloxy, where the organic groups are hydrocarbon radicals selected from the same group as $R^1$. Alternatively, the silicon-bonded hydrogen atoms can be present only at the terminal positions of the organopolysiloxane molecule.

Hydrocarbon radicals that can be represented by $R^1$ in the foregoing formulae for the organohydrogensilanes and organohydrogensiloxanes that are reacted with the propargyl ester of formula 3 include but are not limited to alkyl containing from 1 to about 10 carbon atoms, cycloalkyl, aryl, alkaryl, aralkyl and substituted alkyl radicals, where the substituent is preferably a halogen atom. $R^1$ is preferably methyl, phenyl, or 3,3,3-trifluoropropyl, this preference being based on the availability of the corresponding chlorosilanes used to prepare the organohydrogensilanes and organohydrogensiloxanes.

The organosilicon products of the hydrosilylation reaction are typically solids at room temperature and can be purified using conventional recrystallization techniques.

The Photoinitiated Crosslinking Reaction of the Present Organosilicon Compounds

As disclosed in a preceding section of this specification, it has been reported that the conjugated sequence of ethylenic double bonds present in the organosilicon compounds of this invention undergoes an intramolecular addition reaction in the presence of ultraviolet radiation in the range from 300 to 400 nanometers (nm). This reaction is reversible in the presence of ultraviolet radiation in the range from 200 to 260 nm, with recovery of typically more than about 50 percent of the initial organosilicon compound.

When the organosilicon portion of the present compounds is an organopolysiloxane or a disiloxane containing 2 or more substituents represented by Q in formula 1 of this specification the product of the intermolecular reaction is a crosslinked material that is insoluble in solvents such as toluene used to dissolve the initial organosilicon compound and the product of the reversed intermolecular addition reaction.

The present inventor discovered that the ability of solutions of the present organosiloxanes to form a insoluble crosslinked material in the presence of ultraviolet radiation makes these organosiloxanes ideal for use as coatings curable by ultraviolet light and as absorbers of ultraviolet radiation.

EXAMPLES

The following examples describe preferred embodiments of the products of this invention and methods for preparing them. The examples should not be interpreted as limiting the scope of the invention as defined in the accompanying claims. Unless otherwise indicated, all parts and percentages are by weight and viscosity values were measured at 25° C. In the formulae Me represents the methyl radical and Ph represents the phenyl radical.

EXAMPLE 1

Preparation of Propargyl Cyanoacetate 1.6 parts of propargyl alcohol and 1 part of cyanoacetic acid were dissolved in 4.7 parts of chloroform. 0.2 parts of a 98 percent by weight solution of aqueous sulfuric acid were added as a catalyst and the resultant mixture was heated for 5.5 hours at a temperature of 61° C. The crude ester was washed with water. Volatile materials were removed using reduced pressure. The propargyl ester of alpha-cyanoacetic acid, $C\equiv NCH_2$-$C(O)OC\equiv CH$, was isolated in 71 percent yield.

EXAMPLE 2

Reaction of Propargyl Cyanoacetate with Cinnamaldehyde to Form Propargyl 2-cyano-5-phenyl-2,4-pentanedienoate (PCCPD, 3a)

A Knoevenagel condensation was conducted by dissolving 15.5 g of the propargyl ester of alpha-cyanoacetic acid, prepared as described in Example 1, in 40 cc of dioxane in an open flask with stirring. An equimolar amount (16.6 g) of cinnamaldehyde was then added to the reaction mixture and the flask cooled in an ice-water mixture. 0.4 cc of piperidine were then gradually over a period of about 10 minutes as a reaction catalyst. A yellow solid precipitated in about 5 minutes. The mixture was stirred briefly, then allowed to remain under ambient conditions for 3.5 hours, at which time the solid was isolated by filtration and washed with water. A 91% yield of crude product melting at 133° C. was obtained. This material was recrystallized from toluene to yield a product melting at 138° C.

The infra-red and proton nuclear magnetic resonance spectra of the recrystallized compound exhibited maxima characteristic of the C≡CH, C≡N, C≡C, C=O, —COO, CH$_2$C≡C and C=C—C=C groups, and was consistent with the expected product, PCCPD, corresponding to formula 3a $$PhCH=CHCH=C(CN)C(O)CH_2C≡CH \tag{3a}$$

EXAMPLE 3

Hydrosilylation of PCCPD with 1,1,3,3-Tetramethyldisiloxane (TMDS)

A 16.7 percent solution of PCCPD in heated toluene was combined with an amount of a platinum hydrosilylation catalyst equivalent to 0.004 weight percent platinum, based on the weight of toluene. The catalyst was a reaction product of hexachloroplatinic acid and sym-tetramethyldivinyldisiloxane that has been diluted with a liquid dimethylvinylsiloxy terminated polydimethylsiloxane in an amount sufficient to achieve a platinum content of 4.2 weight percent. The resultant solution was heated to a temperature of between 70° and 70° C. at which time an amount of 1,1,3,3-tetramethyldisiloxane (TMDS) equivalent to a molar ratio of silicon-bonded hydrogen atoms to C≡C radicals in the PCCPD of 1:1 was added dropwise to the reaction mixture.

Heating of the resultant reaction mixture was continued for an additional four hours following completion of the TMDS addition, at which time the toluene was removed from the reaction mixture under reduced pressure to yield the desired PCCPD/TMDS reaction product as a yellow solid exhibiting a melting point of 78° C. The IR absorption spectrum of this product exhibited maxima characteristic of the C≡N, C=O, ≡Si-—O—Si≡ and —CH=CH—CH=CH— groups, which is consistent with a compound corresponding to formula 2a.

$$[PhC=CHCH=C(CN)C(O)OCH_2CH=CHSiMe_2]_2O \tag{2a}$$

where Ph represents a phenyl radical and Me represents a methyl radical.

EXAMPLE 4

Preparation of the Reaction Product of Propargyl Ester 3a and an Organohydrogenpolysiloxane (9238-128)

5 g. of propargyl ester 3a was dissolved in 80 cc of toluene by heating at 60° C. 0.02 g. of the platinum catalyst described in Example 1 was then added to the resultant solution, which was placed in a glass reactor equipped with a stirrer, water cooled condenser, addition funnel and thermometer. A solution prepared by dissolving 15.35 g. of a trimethylsiloxy-terminated dimethylsiloxane/methylhydrogensiloxane copolymer in 20 cc of toluene was placed in the addition funnel and about 1 cc of this solution added to the mixture in the reactor. The copolymer exhibited an average degree of polymerization of 100 and contained an average of 10 mol percent of methylhydrogensiloxane units.

The reaction mixture was heated at the boiling point (about 110° C.) as the solution in the addition funnel was added over a period of 2 hours. Heating was continued for an additional 72 hours. At this time the infra-red absorption spectrum of the reaction product indicated that substantially all of the propargyl groups had reacted with substantially all of the silicon-bonded hydrogen atoms present on the dimethylsiloxane/methylhydrogensiloxane copolymer to form an organsiloxane compound of this invention in the form of a trimethylsiloxy-terminated copolymer containing dimethylsiloxane units and units of the formula 2a $$\begin{array}{c} Me \\ | \\ -SiO- \\ | \\ A \end{array} \tag{2a}$$

in place of the original methylhydrogensiloxane units, where A represents PhCH=CHCH=C(C≡N)-C(O)OCH$_2$CH=CH.

The reaction mixture was then combined with a quantity of activated charcoal and filtered. The toluene was removed from the resultant filtrate under reduced pressure to isolate the copolymer.

The utility of this copolymer as a photocurable coating was demonstrated by dissolving a portion of polymer A in isopropanol to form a 5 to 10 percent by weight solution and coating the solution on the surface of a glass microscope slide. A portion of the coating was covered using a patterned mask that allowed the uncovered portion to be exposed to an ultraviolet light source having a wavelength range of from 300 to 450 nanometers and an intensity at the surface of the coating of about 68 milliwatts/cm$^2$ for the period of time, in seconds (?), listed in the following table 1. The coated slide was located 2.5 inches (6.35 cm) from the lamp. The amount of ultraviolet radiation (in millijoules/cm$^2$) to which the sample was exposed is recorded in Table 1.

Following the exposure period the mask was removed from the surface of the coating and the coated surface dipped into isopropanol, which dissolves the uncured coating. The quality of the image remaining of the glass slide was rated on a scale of increasing quality as poor, acceptable or good.

TABLE 1

| Exposure Time (Seconds) | mJ/cm$^2$ | Quality |
|---|---|---|
| 1 | 68 | Poor |
| 1.5 | 102 | Acceptable |
| 2 | 136 | Acceptable |
| 3 | 204 | Good |
| 4 | 272 | Good |
| 6 | 408 | Good |

That which is claimed is:

1. An organosilicon compound selected from the group consisting of silanes corresponding to the molecular formula $$QR^1_3Si$$

and organosiloxanes containing units of the formula $$QR^1_aSiO_{(3-a)/2}$$

where Q represents the radical $$R^2(CH=CH)_n—CH=CR^3C(O)OCH_2CH=CH—,$$

each R$^1$ is individually selected from the group consisting of unsubstituted and substituted monovalent hydrocarbon radicals, R$^2$ represents an aryl, alkoxyaryl or alkaryl radical, R$^3$ is —C≡N or —C(O)OR$^4$ where R$^4$ is hydrogen or an unsubstituted monovalent hydrocarbon radical; a is 0, 1 or 2; and n is 0 or a positive integer, with the proviso that n can be 0 only when $R^2$ represents a naphthyl radical.

2. An organosilicon compound according to claim 1 where $R^1$ is selected from the group consisting of alkyl radicals containing from 1 to 10 carbon atoms, cycloalkyl, aryl, alkaryl, aralkyl and substituted alkyl radicals containing from 1 to 10 carbon atoms where the substituent is a halogen atom; $R^2$ represents phenyl, o-, m-, or p-methoxyphenyl or naphthyl; and $R^4$ is hydrogen.

3. A compound according to claim 2 where $R^1$ is methyl, phenyl, or 3,3,3-trifluoropropyl; $R^3$ is a cyano group; either n is 0 and $R^2$ is naphthyl or n is 1 or 2 and $R^2$ is phenyl; and a is 1 or 2.

4. A method for preparing organosiloxane compounds containing at least one unit represented by the formula $$QR^1{}_aSiO_{(3-a)/2}$$

where Q represents the radical $$R^2(CH{=}CH)_n{-}CH{=}CH{-}CH{=}CR^{3-}C(O)OCH_2CH{=}CH{-},$$

each $R^1$ is individually selected from the group consisting of unsubstituted and substituted monovalent hydrocarbon radicals; $R^2$ represents an aryl, alkoxyaryl or alkaryl radical; a is 0, 1 or 2; n is 0 or a positive integer and $R^3$ represents $-C{\equiv}N$ or $-C(O)OR^4$ where $R^4$ is hydrogen or an unsubstituted monovalent hydrocarbon radical; with the proviso that n can be 0 only when $R^2$ is naphthyl, said method comprising reacting a propargyl ester of the formula $$R^2(CH{=}CH)_nCH{=}C(R^3)C(O)OCH_2C{\equiv}CH$$

with an organohydrogensiloxane containing at least one unit of the formula $$R^1{}_aHSiO_{(3-a)/2}$$

in the presence of a catalytically effective amount of platinum-containing hydrosilylation catalyst.

5. A method according to claim 4 where
$R^1$ is selected from the group consisting of alkyl radicals containing from 1 to 10 carbon atoms, cycloalkyl, aryl, alkaryl, aralkyl and substituted alkyl radicals containing from 1 to 10 carbon atoms, where the substituent is a halogen atom;
$R^2$ is selected from the group consisting of phenyl, o-, m-, and p-methoxyphenyl and naphthyl;
said hydrosilylation catalyst is chloroplatinic acid;
the reaction of said propargyl ester with said organohydrogensiloxane is conducted at a temperature of from 70° to 110° C. in the solvent selected from the group consisting of liquid aromatic and saturated aliphatic hydrocarbons;
and said propargyl ester is prepared using a base-catalyzed condensation reaction between an aldehyde of the formula $R^2(CH{=}CH)_nC(O)H$ and a propargyl ester reactant of the formula $R^3CH_2C(O)OCH_2C{\equiv}CH$.

6. A method according to claim 5 where $R^1$ is methyl, phenyl, or 3,3,3-trifluoropropyl; $R^3$ is a cyano group; and said aldehyde is selected from the group consisting of cinnamaldehyde, and the product of an aldol condensation between an ethylenically unsaturated aliphatic aldehyde and an aromatic aldehyde selected from the group consisting of benzaldehyde, naphthaldehyde and cinnamaldehyde.

7. A method according to claim 6 where said unsaturated aliphatic aldehyde is crotonaldehyde or acrolein.

8. A method for preparing an organosilane represented by the formula $$QR^1{}_3Si$$

where Q represents the radical $$R^2(CH{=}CH)_nCH{=}CR^3C(O)OCH_2CH{=}CH{-};$$

each $R^1$ is individually selected from the group consisting of unsubstituted and substituted monovalent hydrocarbon radicals, $R^2$ represents an aryl, alkoxyaryl or alkaryl radical; a is 0, 1 or 2; n is 0 or a positive integer and $R^3$ represents $-C{\equiv}N$ or $-C(O)OR^4$ where $R^4$ is hydrogen or an unsubstituted monovalent hydrocarbon radical, with the proviso that n can be 0 only when $R^2$ is naphthyl, said method comprising reacting a propargyl ester of the formula $$R^2(CH{=}CH)_nCH{=}CR^3C(O)OCH_2C{\equiv}CH$$

with a triorganohydrogensilane of the formula $$HR^1{}_3HSi$$

in the presence of a catalytically effective amount of platinum-containing hydrosilylation catalyst.

9. A method according to claim 8 where
$R^1$ is selected from the group consisting of alkyl containing from 1 to 10 carbon atoms, cycloalkyl, aryl, alkaryl, aralkyl and substituted alkyl radicals containing from 1 to 10 carbon atoms, where the substituent is a halogen atom;
$R^2$ is selected from the group consisting of phenyl, o-, m-, and p-methoxyphenyl and naphthyl;
said hydrosilylation catalyst is chloroplatinic acid;
the reaction of said propargyl ester with said organohydrogensilane is conducted at a temperature of from 70° to 110° C. in a solvent selected from the group consisting of liquid aromatic and saturated aliphatic hydrocarbons;
and said propargyl ester is prepared using a base-catalyzed condensation reaction between an aldehyde of the formula $R^2(CH{=}CH)_nC(O)H$ and a propargyl ester reactant of the formula $R^3CH_2C(O)OCH_2C{\equiv}CH$.

10. A method according to claim 9 where $R^1$ is methyl; phenyl, or 3,3,3-trifluoropropyl; $R^3$ is a cyano group, and said aldehyde is selected from the group consisting of cinnamaldehyde, and the product of an aldol condensation between an ethylenically unsaturated aliphatic aldehyde and an aromatic aldehyde selected from the group consisting of benzaldehyde, naphthaldehyde and cinnamaldehyde.

11. A method according to claim 10 where said unsaturated aliphatic aldehyde is crotonaldehyde or acrolein.

12. A propargyl ester of the formula $$R^2(CH{=}CH)_n{-}CH{=}CR^3C(O)OCH_2C{\equiv}CH$$

where $R^2$ represents an aryl, alkoxyaryl or alkaryl radical; $R^3$ is $-C{\equiv}N$ or $-C(O)OR^4$, where $R^4$ is hydrogen or an unsubstituted monovalent hydrocarbon radical; and n is 0 or a positive integer, with the proviso that n can be 0 only when $R^2$ represents a naphthyl radical.

13. A propargyl ester according to claim 12 where n is 0 and $R^2$ represents naphthyl, or n is 1 or 2 and $R^2$ represents phenyl; and $R^3$ is $-C{\equiv}N$.

* * * * *